US006576104B1

United States Patent
Nasu et al.

(10) Patent No.: US 6,576,104 B1
(45) Date of Patent: Jun. 10, 2003

(54) APPARATUS AND METHOD FOR READING GEL ELECTROPHORESIS PATTERN

(75) Inventors: Hisanori Nasu, Yokohama (JP); Yoshitaka Nakamura, Chiba (JP); Hitoshi Fujimiya, Mobara (JP); Kenji Yamamoto, Kashiwa (JP)

(73) Assignee: Hitachi Engineering Software Co., Ltd., Kanagawa-ken (JP)

( * ) Notice: Subject to any disclaimer, the term of this patent is extended or adjusted under 35 U.S.C. 154(b) by 0 days.

(21) Appl. No.: 08/212,818

(22) Filed: Mar. 15, 1994

(30) Foreign Application Priority Data

Mar. 15, 1993 (JP) ............................. 5-078569

(51) Int. Cl.⁷ .......................... G01N 27/26; C25B 7/00; C25B 15/00
(52) U.S. Cl. ...................... 204/451; 204/452; 204/455; 204/456; 204/461; 204/601; 204/603; 204/605; 204/606; 204/612
(58) Field of Search ........................ 204/182.8, 299 R, 204/601, 603, 451, 452, 455, 456, 461, 605, 606, 612

(56) References Cited

U.S. PATENT DOCUMENTS 4,936,974 A * 6/1990 Rose et al. ............. 204/299 R
5,180,479 A * 1/1993 Rose, Jr. ................. 204/299 R
5,616,228 A * 4/1997 Nasu et al. ................. 204/603

FOREIGN PATENT DOCUMENTS

DE 3926687 2/1991
EP 49788 8/1992
JP 61-173158 8/1986

OTHER PUBLICATIONS

S–I. Kobayashi et al, "Determination of Fluorescent Compounds by High Performance Liquid Chromatography with Chemiluminescence Detection", Analytical Chemistry, vol. 52, No. 3, Mar. 1990, pp. 424–427.

T. Tsuda et al, "Post–Column Detection for Capillary Zone Electrophoresis", Journal of Chromatography, vol. 456, 1988, pp. 375–381.

H. Swerdlow et al, "Capillary Gel Electrophoresis for Rapid, High Resolution DNA Sequencing", Nucleic Acids Research, vol. 18, No. 6, 1990, pp. 1415–1419.

L.M. Smith et al., "Fluorescence Detection in Automated DNA Sequence Analysis", Nature, vol. 321, Jun. 12, 1986, pp. 674–679.

Kobayashi et al., "Determination of Fluorescent Compounds by HPLC with Chemiluminescence Detection", *Analyt. Chem* vol. 52, No. 3, Mar. 1990, pp. 424–427.*

Tsuda et al., "Post–Column Detection for Capillary Zone Electrophoresis", *J. of Chromat.*, vol. 456, 1988, pp. 375–381.*

* cited by examiner

*Primary Examiner*—Dwayne C. Jones
*Assistant Examiner*—C. Delacroix-Muirheid
(74) *Attorney, Agent, or Firm*—Mattingly, Stanger & Malur, P.C.

(57) ABSTRACT

An apparatus and a method for reading a gel electrophoresis pattern can read the gel electrophoresis pattern of a sample, such as a nucleic acid and a protein, with high sensitivity and without requiring the use of an expensive device structure such as a laser light source of unique type. The gel electrophoresis apparatus is structured by a sample supplying section for supplying a sample labeled with a fluorescent substance from an inlet side of an electrophoresis gel unit; an electrophoresis unit for subjecting the sample to electrophoresis by applying an electrophoresis voltage to the electrophoresis gel unit; a carrying section for withdrawing the electrophoresed sample continually from an outlet side of the electrophoresis gel unit into a carrying fluid and carrying the fluid a predetermined distance; a mixing unit for mixing the carrying fluid with a luminous liquid; and a light receiving section for receiving fluorescence emitted from the sample in the luminous liquid at a position to which the carrying fluid has been carried the predetermined distance.

16 Claims, 3 Drawing Sheets

US 6,576,104 B1

APPARATUS AND METHOD FOR READING GEL ELECTROPHORESIS PATTERN

BACKGROUND OF THE INVENTION

1. Field of the Invention

The present invention relates to an apparatus and a method for reading a gel electrophoresis pattern and, more particularly, to a gel electrophoresis pattern reading apparatus and a gel electrophoresis pattern reading method so adapted as to read a gel electrophoresis pattern with high sensitivity to detection of the electrophoresis pattern without requiring any expensive device configuration such as a special laser light source, the gel electrophoresis pattern being obtained by subjecting a sample containing nucleic acids or protein acids to electrophoresis in gel and separating the sample from the gel material.

2. Description of the Related Art

Heretofore, techniques for analysis by means of gel electrophoresis methods have been extensively utilized for the fragmentation and for the analysis of structures of protein acids and nucleic acids present as a polymer in the body of an animal or plant. The gel electrophoresis method has the advantage that a minute amount of a sample can be analyzed in an appropriate manner so that in many cases the gel electrophoresis method is utilized for experiments in which a sample can be procured in a very limited amount. Therefore, the analysis using the gel electrophoresis method requires a very high sensitivity to detection of the sample.

In conventional techniques, a sample to be analyzed is first labelled with a radioactive isotope, the labelled sample is injected into a gel, and the resulting gel material is subjected to electrophoresis. After the gel electrophoresis, the gel is attached to an X-ray film or the like for exposure to X rays to be emitted from the radioactive isotope labelled in the sample. After exposure of the gel material containing the labelled sample to the X-ray film or the like for a given period of time, the X-ray film is then developed, and the exposed pattern resulting from the radioactive isotope transcribed onto the X-ray film is read as a gel electrophoresis pattern in order to analyze the structures of the proteins or nucleic acids of the sample.

The radioactive isotopes, however, are so hazardous that they should be handled and managed with extreme care and with high security. Recently, techniques for handling laser light and technologies of laser light sources, optical sensors and signal processing have greatly developed leading to the development of fluorescence detecting methods for detecting an electrophoresis pattern without requiring the use of such hazardous radioactive isotopes. The fluorescence detecting methods comprise labelling a sample with a fluorescent substance, subjecting the sample to electrophoresis, exciting the labelled fluorescent substance directly with a laser light source, and detecting the resulting fluorescent pattern, thereby resulting in the detection of the electrophoresis pattern.

As an example of reading an electrophoresis pattern by the fluorescence detecting method, which has initially been developed, there is known a method for determining the sequence of a DNA as disclosed in Japanese Patent Unexamined Publication Kokai No. 61-173,158. An outline of a fluorescence detecting method utilized for the DNA sequence determining method will be described with reference to FIGS. 4 and 5, showing a schematic representation of the method for the detection of a gel electrophoresis pattern by the fluorescence detecting method, in which FIG. 4 is a block diagram showing an outline of a gel electrophoresis apparatus and FIG. 5 shows the details of a portion of a fluorescence detecting section of the gel electrophoresis apparatus of FIG. 4.

First, a description will be made of the device structure of the gel electrophoresis apparatus with reference to FIG. 4. The gel electrophoresis apparatus comprises a gel material 31 in which electrophoresis is to be conducted, a fine tube 32 for retaining the gel material 31, an upper buffer solution container or tank 33 and a lower buffer solution container or tank 34, between which an electrical field is applied to the gel material 31 held in the fine tube 32, a first electrode 35a, a second electrode 35b, a light source 36 for exciting a fluorescent substance labelled in the electrophoresed sample, a detector 37 for detecting the fluorescence emitted from the sample, a data processing section 38 for processing signals transmitted from the detector 37 and converting the fluorescent signals into electrical signals, and an electric power source 39 for applying the electrophoresis electrical field between the first electrode 35a and the second electrode 35b.

Next, an operation of the gel electrophoresis apparatus will be described by example where a DNA sample is electrophoresed as an object of electrophoresis and an electrophoresis pattern of the DNA sample is read with the gel electrophoresis apparatus. The DNA sample is first labelled with a fluorescent substance and the labelled sample is poured into the upper buffer solution container 33 from which the sample in turn is introduced into the fine tube 32, and an electrophoresis voltage of from several kV to approximately 10 kV is applied from the electric power source 39 between the first and second electrodes 35a and 35b. As the DNA has negative charges, they migrate toward the positive electrode of the second electrode 35b upon application of such electrophoresis voltage and they eventually reach the position of the light source 36. Thereafter, the fluorescent substance labelled in the DNA sample is excited in this position upon exposure to laser beams emitted from the light source 36, thereby emitting fluorescence that in turn is detected and received by the detector 37. The fluorescence received by the detector 37 is then converted into electrical signals and the detector 37 transmits the electrical signals to the data processing section 38 which in turn processes the electrical signals and determines the sequences of the DNA fragments separated by their molecular weights, thereby yielding an electrophoresis pattern.

The detector 37 is arranged such that the fluorescence emitted from the sample in the gel material 31 migrating within the fine tube 32 can be received in a manner as shown in FIG. 5, which is a partially transverse sectional view (looking down). As shown in FIG. 5, when the sample migrates downward through the gel material 31 and the sample reaches the position of the fine tube 32 which is irradiated with laser beams 40 emitted from the light source 36, the fluorescent substance labelled in the DNAs of the sample is excited with the laser beams 40, thereby resulting in the emission of fluorescence 41 that in turn is received by the detector 37. The received fluorescence 41 is then transmitted to a photomultiplier of the detector 37 and the photomultiplier converts the fluorescence 41 into electrical signals and transmits the electrical signals to the data processing unit 38. The data processing unit 38 is arranged such that the sequences of the DNA fragments in the sample are determined by the molecular weights on the basis of the peak positions of the intensity of the fluorescence 41 emitted from the DNA sample and received by the detector 37.

When they are employed as a sample, DNA fragments are labelled with the fluorescent substance so as to have different fluorescent wavelengths corresponding to their ingredients, i.e. four bases comprising adenine, cytosine, guanine and thymine, and to determine the DNA sequences of the four bases simultaneously by causing the DNA sample to migrate down through only one fine tube. The fluorescent substance with which to label the DNA fragments, which can emit four different fluorescent wavelengths, may include, for example, fluorescein isothiocyanate (FITC), rhodamine isothiocyanate (EITC), tetramethylrhodamine isothiocyanate (TMRITC), and substituted rhodamine isothiocyanate (XRITC), respectively. Further, the gel electrophoresis apparatus of this type has a sensitivity to detection of DNAs in the order of $1\times10^{-16}$ mole as high as the method using radioactive isotopes, when argon ion laser having a wavelength of 488 nm or 514 nm is employed.

In addition, Japanese Patent Unexamined Publication Kokai No. 61-173,158 briefly alludes to an example in which luminescence can be caused by taking advantage of chemical reaction energy. The example does not specifically disclose any procedures of the elution from a gel material, a reaction with a luminous substance, the removal of an unnecessary labelling substance, and the like. Actually, many specific problems should be solved in embodying techniques utilizing luminescence based on the chemical reaction energy in a device structure. Such problems may include, for example, procedures for the supply of a source of chemically light-emitting energy, the mixture of the luminous substance with a labelling substance, and the removal of the labelling substance after luminescence in order to prevent background noise from being caused by residual substances.

The electrophoresis methods can be applied to, for example, the diagnosis of hereditary diseases, the investigation of DNAs in determining suspects of crimes and the investigation of the relationship between a parent and a child, in addition to the determination of the DNA sequence. In the diagnosis of hereditary diseases, it is currently possible to distinguish even one base from samples on the basis of the difference between the electrophoresis patterns by taking advantage of the difference in the structure of a high dimension under specific conditions (e.g. time or pH as causing a minute difference in denatured states of DNA) by the substitution of the base or bases inherent in each hereditary disease, such as single strand conformation polymorphism. On the other hand, the investigation of DNA in, for example, determining a suspect of crime and a parent-child relationship is made by comparing the difference in electrophoresis distances by taking advantage of a deviation in DNAs (polymorphism) between individuals.

In such experiments, the base length of a DNA is approximately 1,000 bases or less in many cases, and the gel material to be frequently employed for electrophoresis is polyacrylamide gel. In the case of the base length of a DNA of several thousands of bases, agarose gel is usually employed. Further, a gel electrophoresis apparatus of a flat plate type is employed for the comparison of the electrophoresis pattern of a sample with a reference DNA electrophoresis pattern. With such a gel electrophoresis apparatus, the sample and the reference DNA sample are subjected to gel electrophoresis side by side for a ready reference to the difference between the two electrophoresis patterns.

These methods, however, require care in, for example, sustaining homogeneity of a gel material with high stability and maintaining the uniformity of temperature on the electrophoresis plates during electrophoresis processes. In particular, very careful management of temperature using a thermostat is required in single strand conformation polymorphism. The management of temperature makes the cost of a device expensive and its size large because the electrophoresis apparatus of a flat plate type consumes a large amount of power and the amount of heat evolved is great. On the other hand, such problems inherent in the electrophoresis apparatus of the flat plate type can be solved by an electrophoresis apparatus of a capillary type because such a capillary-type electrophoresis apparatus can make its electrophoresis section smaller in size and it can be handled in a manner easier than that of the flat plate type.

However, the prior art electrophoresis apparatus so adapted as to read the electrophoresis pattern obtained by the fluorescence detecting method of conventional technology requires the use of a laser light source of a unique type corresponding to the wavelength at which the fluorescent substance is to be excited. The conventional electrophoresis apparatus suffers from various disadvantages. The cost of the laser light source, which accounts for most of the total cost of the apparatus, is so great that the cost of the apparatus itself becomes expensive as well. Further, laser light should be handled with great care because the laser light emitted from the laser light source has a high energy density even if it would scatter, so that there is the risk of causing disorders or abnormality of vision, such as dyschromatopsia or blindness, if the laser light would enter the naked eye. Hence, such a laser light source is to be incorporated in the electrophoresis apparatus with great attention paid to security from such laser light. This also leads to making the electrophoresis apparatus expensive.

SUMMARY OF THE INVENTION

The primary object of the present invention is to provide an apparatus for reading an electrophoresis pattern, which can be prepared at cheaper costs and handled in an easier fashion than conventional electrophoresis apparatuses.

The present invention has another object to provide a method for reading an electrophoresis pattern which allows for easier handling than conventional electrophoresis apparatuses.

The present invention has a further object to provide an apparatus for reading an electrophoresis pattern, which does not require an expensive device structure, including the use of a laser light source of a unique type.

The present invention has a still further object to provide a method for reading an electrophoresis pattern, which can read the electrophoresis pattern with higher sensitivity to detection of a sample than conventional electrophoresis apparatuses.

In order to achieve the objects as described hereinabove, the present invention consists of an apparatus for reading an electrophoresis pattern, which comprises: a sample supplying means for supplying a sample labelled with a fluorescent substance from an inlet side of an electrophoresis gel unit; an electrophoresis means for subjecting the sample to electrophoresis by applying an electrophoresis voltage to the electrophoresis gel unit; a carrying means for withdrawing the electrophoresed sample continually from an outlet side of the electrophoresis gel unit into a carrying fluid and carrying the carrying fluid a predetermined distance; a mixing means for mixing the carrying fluid with a luminous liquid or solution; and a light receiving means for receiving fluorescence emitted from the sample in the luminous liquid at a position to which the carrying fluid has been carried or transferred the predetermined distance.

In another aspect of the present invention, the apparatus for reading the gel electrophoresis pattern further comprises a bypass means for removing gases generated from an electrophoresis electrode disposed at the outlet side of the electrophoresis gel unit by bypassing a flow path through which the carrying fluid passes.

In a further aspect of the present invention, the gel electrophoresis pattern reading apparatus is arranged such that the carrying fluid is a liquid having a composition equivalent or similar to a buffer solution placed at the electrode side on the inlet side of the electrophoresis gel unit, wherein the luminous liquid or solution is capable of causing the fluorescent substance of the sample to emit fluorescence upon a chemical reaction with a peroxalic acid.

In a still further aspect of the present invention, the apparatus for reading the gel electrophoresis pattern comprises: an electrophoresis gel unit which is filled with gel material and in which electrophoresis is to be conducted; a first fine tube which is filled with the gel unit; a buffer solution container or tank for storing a buffer solution disposed so as for the buffer solution to come in contact with each of both ends of the gel unit disposed in the first fine tube; an electrode disposed so as to come into contact with the buffer solution in the buffer solution container or tank; a power source for applying electrophoresis voltage to the electrode; a second fine tube for carrying or transferring the electrophoresed sample separated while supplying the buffer solution; a third fine tube for supplying a luminous liquid; a mixer for mixing the solution withdrawn from the second fine tube with the liquid supplied from the third fine tube; a fourth fine tube for withdrawing the mixture from the mixer and allowing a chemical reaction to be carried out with the luminous liquid for a predetermined period of time so as to emit fluorescence to a sufficiently high intensity; a fluorescence detector disposed at a terminal end portion of the fourth fine tube for detecting the fluorescence emitted from the mixture; and a data processing unit for processing electrical signals converted from the fluorescence detected by the fluorescence detector.

In an additional aspect, the present invention consists of a method for reading an electrophoresis pattern, which comprises: supplying a sample labelled with a fluorescent substance from an inlet side of the electrophoresis gel unit; subjecting the sample to electrophoresis by applying an electrophoresis voltage to the electrophoresis gel unit; withdrawing the electrophoresed sample continually from an outlet side of the electrophoresis gel unit into a carrying fluid and carrying or transferring the carrying fluid a predetermined distance; mixing the carrying fluid with a luminous liquid; and receiving fluorescence emitted from the sample upon a chemical reaction in the luminous liquid at a position to which the carrying fluid has been carried the predetermined distance.

With the arrangement of the apparatus for reading the gel electrophoresis pattern in accordance with the present invention, the electrophoresis means is arranged to subject the sample to electrophoresis by applying the electrophoresis voltage to the electrophoresis gel unit when the electrophoresis gel unit is supplied with the sample labelled with a fluorescent substance by the sample supplying means. Further, the carrying means is arranged for withdrawing the electrophoresed sample into the carrying fluid continually from the outlet side of the electrophoresis gel unit and carrying the withdrawn fluid. The carrying fluid containing the electrophoresed sample, which is carried or transferred by the carrying means, is then mixed with the luminous liquid by the mixing means. In the carrying fluid containing the electrophoresed sample, an intermediate active substance or material produced as a result of a chemical reaction with the luminous liquid can excite the fluorescent substance labelled in the sample, thereby causing fluorescence to emit from the sample. The light receiving means is so disposed as to receive the fluorescence at the position to which the carrying fluid is carried or transferred over a predetermined period of time, until the fluorescent substance is excited so as to emit a sufficiently high intensity of fluorescence, in the path through which the carrying fluid is transferred and fluorescence is caused to be emitted from the fluorescent substance, that is, to which the carrying fluid is transferred a predetermined distance.

In the arrangement of the apparatus for reading the gel electrophoresis pattern in accordance with the present invention, no laser light is employed as the light for exciting the fluorescent substance of the electrophoresed sample and, for example, the intermediate active substance or material produced as a result of a chemical reaction with the luminous liquid capable of luminescence is employed in place of such laser light. The energy of the intermediate active substance or material is transmitted to the fluorescent substance and can exert the action of exciting the fluorescent substance in the sample to a sufficient extent. As a result, the fluorescent substance is excited, thereby evolving fluorescence to an intensity high enough to allow a detector of usual type to detect the electrophoresis fluorescence pattern with sufficiently high sensitivity.

The apparatus for reading the gel electrophoresis pattern according to the present invention may be provided with the bypassing means which in turn is so adapted as to remove the gases generated from the electrophoresis electrode on the outlet side of the electrophoresis gel unit by bypassing the path through which the carrying fluid flows. When the electrophoresis voltage is applied to the electrophoresis gel unit in order to subject the sample to electrophoresis, the gases are produced as a result of electrophoresis. If they are accumulated on the outlet side of the electrophoresis gel unit, the gases may act as a factor adversely affecting the electrophoresis so that they are required to be removed by the bypassing means. Further, the gases may disturb the flow of the carrying fluid in withdrawing the electrophoresed sample continually from the outlet side of the electrophoresis gel unit by means of the carrying means. Hence, the gases may act as a factor that disturbs the conveyance of the electrophoresed sample together with the carrying fluid so that the gases are to be removed by the bypassing means before the carrying fluid is carried.

The carrying fluid to be employed for this invention may be a liquid having a composition substantially identical to or similar to that of the buffer solution to be supplied from the inlet side of the electrophoresis gel unit. Hence, the carrying fluid can be utilized, too, as the buffer solution to be supplied to the inlet side of the electrophoresis gel unit. In this case, the electrophoresed sample separated from the gel unit is discharged from the outlet side of the electrophoresis gel unit into the carrying fluid. Then, the carrying fluid containing the electrophoresed sample is then carried or transferred intact.

For the apparatus for reading the gel electrophoresis pattern in accordance with the present invention, there may be employed, as the luminous liquid, a liquid capable of a chemical reaction with a peroxalic acid ester. The peroxalic acid ester can produce the intermediate active substance or material during the reaction with the fluorescent substance and can provide the fluorescent substance with its energy to thereby emit fluorescence. The amount or extent of the emission of fluorescence can readily be adjusted by adjusting the reaction of producing the intermediate active substance or material, and the amount of fluorescence for exciting the fluorescent substance can be adjusted by adjusting the reaction time.

In the method for reading the gel electrophoresis pattern in accordance with the present invention, the sample labelled with the fluorescent substance is supplied from the inlet side of the electrophoresis gel unit, the sample is subjected to electrophoresis by applying the electrophoresis voltage to the electrophoresis gel unit, the electrophoresed sample is withdrawn from the outlet side of the electrophoresis gel unit continually into the carrying fluid, the carrying fluid is then mixed with the luminous liquid, the carrying fluid is transferred the predetermined distance, and the fluorescence emitted from the sample in the carrying fluid is received.

Hence, the method according to the present invention can continually carry out the process for supplying the sample labelled with the fluorescent substance to the electrophoresis gel unit, the process for subjecting the sample to electrophoresis in the electrophoresis gel unit, the process for exciting the fluorescent substance in the sample electrophoresed in and separated from the electrophoresis gel unit, and the process for receiving fluorescence emitted from the fluorescent substance of the sample while transferring the carrying fluid containing the sample. The arrangement of the method can continually read electrophoresis patterns of the sample.

Other objects, features, and advantages of this invention become apparent in the course of the description of the preferred embodiments which follows, with reference to the accompanying drawings.

DETAILED DESCRIPTION OF THE PREFERRED EMBODIMENTS

The present invention will be described in more detail by way of examples with reference to the accompanying drawings.

Figure 1:
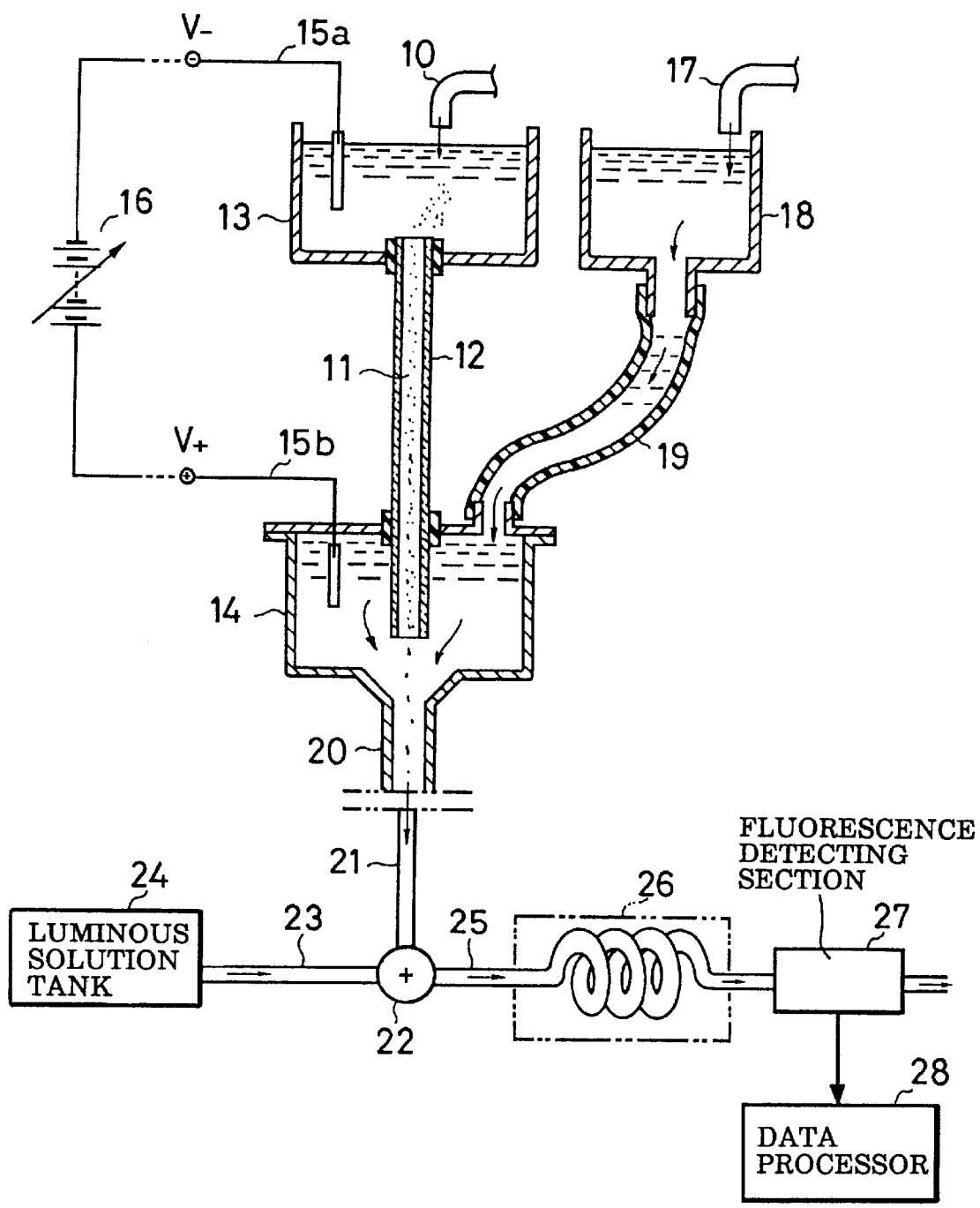
FIG. 1 is a block diagram showing an overall device structure of an apparatus for reading an electrophoresis pattern according to an embodiment of this invention.

FIG. 1 shows an overall device structure of an apparatus for reading an electrophoresis pattern according to an embodiment of this invention. In FIG. 1, reference numeral 10 denotes a sample supplying section for supplying a sample; reference numeral 11 an electrophoresis gel unit in which to carry out electrophoresis for the sample; reference numeral 12 a fine tube; reference numeral 13 an upper buffer solution container; reference numeral 14 a lower buffer solution container; reference symbol 15a a first electrode; reference symbol 15b a second electrode; reference numeral 16 an electric power; source reference numeral 17 a carrying-fluid supplying section for supplying a carrying fluid; reference numeral 18 a solution container; reference numeral 19 a carrying-fluid supplying tube through which to supply the carrying fluid; reference numeral 20 an outlet for withdrawing the carrying fluid; reference numeral 21 a first carrying fine tube; reference numeral 22 a mixer; reference numeral 23 a tube for supplying a luminous liquid; reference numeral 24 a tank or container for storing the luminous liquid; reference numeral 25 a second carrying fine tube; reference numeral 26 a delay section for causing a chemical reaction to be carried out with the luminous liquid so as to emit a sufficiently high intensity of fluorescence; reference numeral 27 a fluorescence detecting section for detecting fluorescence; and reference numeral 28 a data processing unit.

A description will be made of the device structure in accordance with an embodiment of the apparatus of this invention with reference to FIG. 1. The electrophoresis section of the gel electrophoresis apparatus is structured mainly by the electrophoresis gel unit 11 into which the sample is poured and in which the sample is subjected to electrophoresis. The electrophoresis gel unit 11 is filled with gel material and held by the fine tube 12 which in turn is communicated at its upper end portion with the upper buffer solution container or tank 13 and at its lower end portion with the lower buffer solution container or tank 14. In both of the upper buffer solution container 13 and the lower buffer solution container 14, a buffer solution is contained and stored. To the electrophoresis gel unit 11 is applied an electrophoresis voltage with the aid of the buffer solution for subjecting the gel material containing the sample to electrophoresis. To this end, the first electrode 15a is arranged to be located in the buffer solution stored in the upper buffer solution container 13 and the second electrode 15b is arranged to be located in the buffer solution stored in the lower buffer solution container 14, thereby electrically connecting the upper buffer solution container 13 with the lower buffer solution container 14 through the electrophoresis gel unit 11 disposed in the fine tube 12. Further, the electric power source 16 is provided between the first and second electrodes 15a and 15b.

The sample is supplied from the upper end portion of the fine tube 12 filled with the electrophoresis gel unit 11, which is communicated with the upper buffer solution container 13 to which the sample supply section 10 is connected. The sample is first supplied to the buffer solution of the upper buffer solution container 13 and introduced into the electrophoresis gel unit 11 disposed in the fine tube 12. The electrophoresed sample is withdrawn from the lower end portion of the fine tube 12 which is communicated with the lower buffer solution container 14. The sample withdrawn from the fine tube 12 into the lower buffer solution container 14 is then discharged from the outlet 20 disposed at its lower portion, from which the sample is withdrawn together with the carrying fluid filled in the lower buffer solution container 14 and then carried and transferred through the carrying fluid.

The sample electrophoresed in the electrophoresis gel unit 11 and separated therefrom is introduced into the lower buffer solution container 14 and then withdrawn from its outlet 20 together with the carrying fluid. The lower buffer solution container 14 has an opening disposed at its upper portion, which is communicated with the solution container 18 through the carrying-fluid supplying tube 19 to supply the lower buffer solution container 14 with the carrying fluid from the solution container 18. The carrying-fluid supplying tube 19 is arranged so as to allow the carrying fluid to flow at constant flow speed and rate. Further, the solution container 18 is supplied with a predetermined amount of the carrying fluid from the carrying-fluid supplying section 17.

The carrying fluid to be supplied to the lower buffer solution container 14 from the solution container 18 should have a composition capable of acting as the buffer solution for the electrophoresis gel unit 11 as well. In this sense, it is preferred to utilize, as the carrying fluid, one that has substantially the same composition as the buffer solution supplied to the upper buffer solution container 13. It is also possible to use as the carrying fluid one that has a composition different from those and having a higher extent of flowability than those as described hereinabove because the buffer solution in the lower buffer solution container 14 should act as carrying the electrophoresed sample.

The pattern detecting section of the gel electrophoresis apparatus according to the present invention is structured by placing the focus upon the passage through which the carrying fluid withdrawn from the outlet 20 of the lower buffer solution container 14 flows, as shown in FIG. 1. The outlet 20 of the lower buffer solution container 14 is communicated with the first fine tube 21 which in turn is communicated at its downstream end with the first inlet of the mixer 22. The second inlet of the mixer 22 is communicated with the container 24 for storing the luminous liquid through the tube 23 for supplying the luminous liquid through which the luminous liquid is supplied to the mixer 22. The mixer 22 is arranged to mix the buffer solution functioning as the carrying fluid and containing the electrophoresed sample, supplied through its first inlet from the lower buffer solution container 14, with the luminous liquid supplied through its second inlet from the container 24. The mixture is then withdrawn from the outlet of the mixer 22, which is communicated with the second carrying fine tube 25. The fine tube 25 is provided with the delay section 26 which is arranged such that the fluorescent substance in the sample is reacted with the luminous liquid for a time long enough to allow the fluorescent substance to emit a sufficiently high intensity of fluorescence. Then, the mixture with the fluorescence emitting from the fluorescent substance passes through the delay section 26 and is transferred to the fluorescence detecting section 27, which is provided with the photomultiplier for detecting the fluorescence emitted from the fluorescent substance labelled in the electrophoresed sample. The fluorescence detected by the fluorescence detecting section 27 is then converted into electrical signals and the electrical signals are processed by the data processing unit 28.

As the luminous liquid to be supplied to the container 24, there may be employed, for example, a chemically luminous liquid causing a chemical reaction such as chemiluminescence and a luminous substance causing a chemical reaction such as bioluminescence, particularly known as luminescence by fireflies. As the chemiluminescence, there may preferably be employed a chemical reaction with a peroxalic acid ester that can produce an intermediate active substance or material and provide the fluorescent substance with its energy to thereby emit fluorescence. The luminous liquid utilizing the chemical reaction with the peroxalic acid ester can emit fluorescence efficiently for exciting the fluorescent substance labelled in the sample, for example, for use in analyzing DNAs or other substances. The luminous liquid can also provide exciting light having an effective wavelength in the region in which the fluorescent substance can emit fluorescence.

Now, a description will be made of a series of operations to be carried out by the gel electrophoresis apparatus according to the present invention. First, a sample labelled with the fluorescent substance, such as an enzyme causing a chemiluminescence or a luminous substrate, is poured into the upper buffer solution container 13 from the sample supply section 10 and allowed to migrate into the electrophoresis gel unit 11 filled in the fine tube 12. As the fluorescent substance to be employed for labelling the sample in accordance with this invention, there may be employed the fluorescent substances equal to or similar to those fluorescent substances as having hitherto been extensively utilized for analyzing electrophoresis patterns of DNAs and the like, and such substance may specifically include, for example, fluorescein isothiocyanate (FITC), rhodamine isothiocyanate (EITC), tetramethylrhodamine isothiocyanate (TMRITC), and substituted rhodamine isothiocyanate (XRITC).

After the introduction of the sample into the electrophoresis gel unit 11, for example, an electrophoresis voltage of 10 kV is applied from the electric power source 16 across the first electrode 15a and the second electrode 15b, thereby beginning the gel electrophoresis of the sample. During the gel electrophoresis, gases are produced as a side effect of electrolysis at the electrode plate of each of the first and second electrodes 15a and 15b. The gases produced at the first electrode 15a in the upper buffer solution container 13 are allowed to discharge from its upper side. On the other hand, the gases produced at the second electrode 15b in the lower buffer solution container 14 are discharged from its upper portion through the carrying-fluid supplying tube 19 by allowing the gases to be discharged in the direction opposite to the flow of the buffer solution flowing as the carrying fluid through the carrying-fluid supplying tube 19. Further, in order to prevent the gases produced at the side of the second electrode 15b in the lower buffer solution container 14 from staying around the outlet of the fine tube 12, the electrode plate of the second electrode 15b is disposed so as to assume the position above the bottom end gel surface of the electrophoresis gel unit 11 because such gases may act as a factor for disturbing the electrophoresis.

The sample separated from the electrophoresis gel unit 11 by electrophoresis and introduced into the lower buffer solution container 14 is discharged from the outlet 20 disposed at the lower side of the lower buffer solution container 14 along the flow of and together with the buffer solution supplied as the carrying fluid from the carrying-fluid supplying tube 19 into the lower buffer solution container or tank 14. After the passage through the first carrying fine tube 21, the sample is transferred to the mixer 22 where the luminous liquid containing a substrate for chemiluminescence is supplied through the supplying fine tube 23 from the luminous liquid supplying section 24. In the mixer 22, the luminous liquid containing such a substrate is admixed with the sample contained in the carrying fluid. After the admixture in the mixer 22, the mixture is then discharged from the outlet of the mixer 22 into the second carrying fine tube 25 and transferred together with the buffer solution to the delay section 26 where the fine tube constituting the delay section 26 is so arranged as to allow the fluorescent substance to react with the luminous liquid for a sufficiently long period of time to thereby emit fluorescence to an intensity high enough to be detected by the fluorescence detecting section 27. After the detection of the intensity of fluorescence of the sample, the sample is withdrawn from the fluorescence detecting section 27 together with the carrying fluid.

The luminous liquid to be supplied to the mixer 22 through the luminous-liquid supplying tube 23 from the luminous liquid container 24 may contain the substrate for chemiluminescence, such as a mixture of aryl oxalate with acetonitril as a hydrogen peroxide aqueous solvent or an imidazole as an acetoalkali catalyst. The aryl oxalate may include, for example, bis(2,4,6-trichlorophenyl)oxalate (TCPO), bis[4-nitro-2-(3,6,4-trioxadesilloxycarbonyl)-phenyl]oxalate (TDPO) and bis(2.4-dinitrophenyl)oxalate (DNPO).

The fluorescence detecting section 27 comprises an optical filter for selectively allowing a permeation of an objective wavelength, and a photoelectric conversion element. The fluorescence detecting section 27 may have substantially the same structure as fluorescence detectors of conventional technology, and is arranged to detect the fluorescence from the carrying fluid (i.e. the buffer solution containing the sample and the luminous liquid) passing through the fine tube disposed in the detecting section and to convert the detected fluorescence into electrical signals. The fluorescent pattern converted into the electrical signals indicates the electrophoresis pattern of the sample electrophoresed in and separated from the electrophoresis gel unit 11, and the electrophoresis pattern is subjected to data processing by the data processing unit 28 which is so adapted as to determine the peak positions in accordance with the intensity of the fluorescence detected and to determine the sequence of the ingredients of the sample separated by their molecular weights.

The fluorescence detecting section 27 is arranged such that the fluorescence can be detected by allowing the photoelectric conversion element to sense the fluorescence emitted from the sample while passing through the fine tube disposed in the fluorescence detecting section 27 along and together with the flow of the carrying fluid containing the sample with the luminous liquid. In order to improve the efficiency of collecting or gathering the fluorescence, various device structures are possible.

Figure 2:
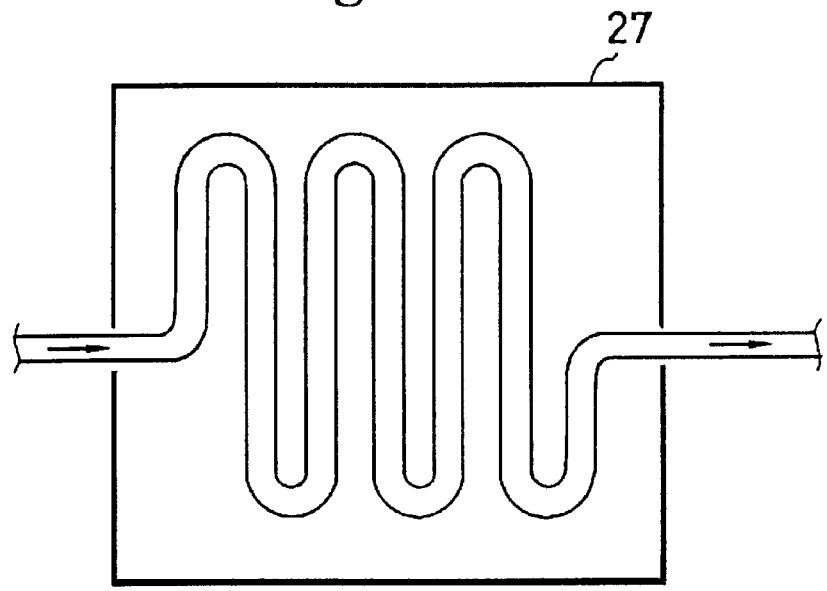
FIG. 2 is a schematic representation showing an example of the structure of a fluorescence detecting section so adapted as to improve efficiency of collecting or gathering light.

FIG. 2 shows the structure of the fluorescence detecting section arranged so as to improve the efficiency in collecting or gathering fluorescence. In this fluorescence detecting section 27, the fine tube is arranged to turn upward and downward alternately in its position in front of the photoelectric conversion element of the detection section, thereby increasing the luminous area of the sample existing in the fine tube relative to the photomultiplier of the photoelectric conversion element. This arrangement of the fluorescence detecting section can detect the fluorescence with high sensitivity. In addition to the vertical zig-zag arrangement of the fine tube as described hereinabove, it is also possible to arrange the fine tube in the fluorescence detecting section in a spiral relationship. The fluorescence detecting section 27 of the gel electrophoresis apparatus according to the present invention can present the advantage that the fluorescence can be detected with sensitivity and ease as high as conventional technology utilizing laser light sources because this arrangement does not require the use of laser light, so that this method for the detection of fluorescence is not affected adversely due to scattering of light.

The material for use in labelling the sample with the fluorescent substance is readily available, various devices of fluorescent type having been developed which can excite the fluorescent substance with laser beams, and which can be applied to this invention without difficulty. Even if the amount of a sample such as DNA fragments is very small, the amount can be amplified with ease to a level necessary for analysis. Such means may include, for example, procedures for amplifying genes utilizing fluorescence-labelled primers or a dideoxy nucleotide, such as a polymerase chain reaction and the like. These methods can covalently bind the fluorescent substance directly with a DNA.

In addition, a description will be made of an example of the method using a pigment for the intercalation into the DNA double strand, as a method other than those capable of covalently bonding the fluorescent substance directly with the DNA sample. Such fluorescent pigments may include, for example, ethdium homodimer, thiazole yellow homodimer, oxazole yellow homodimer, and the like (for example, Nature: Vol. 359 (Oct. 29, 1992), pp. 859–861). These pigments have the feature that they can be intercalated into the DNA double strand merely by mixing them with the DNA fragments as the sample. Once intercalated, they are unlikely to be removed from the sample so that no chemical processing is required for labelling and experiments can be done efficiently.

Figure 3A:
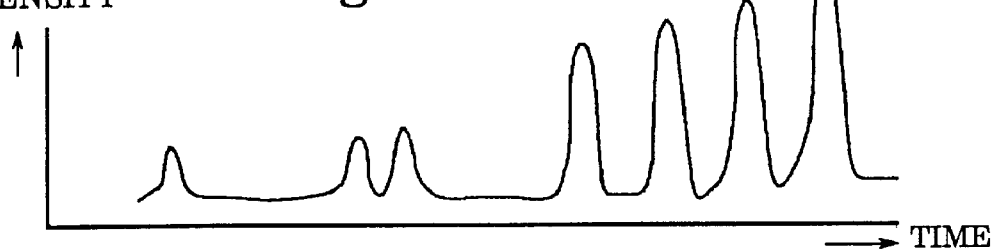
FIGS. 3a and 3b are graphs showing a variation in intensity of fluorescence relative to the progress of time when a reference marker and a DNA sample are subjected to electrophoresis, respectively, for preparing an electrophoresis pattern.
Figure 3B:
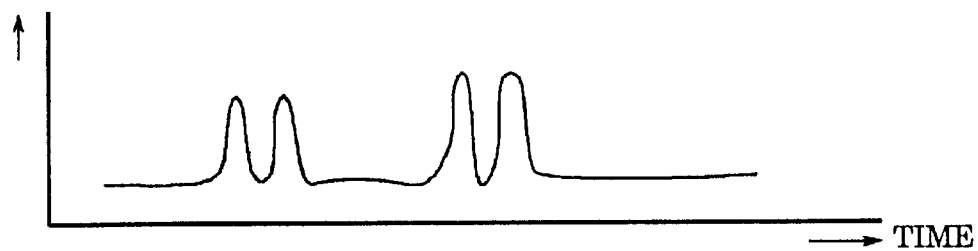
Figure 4:
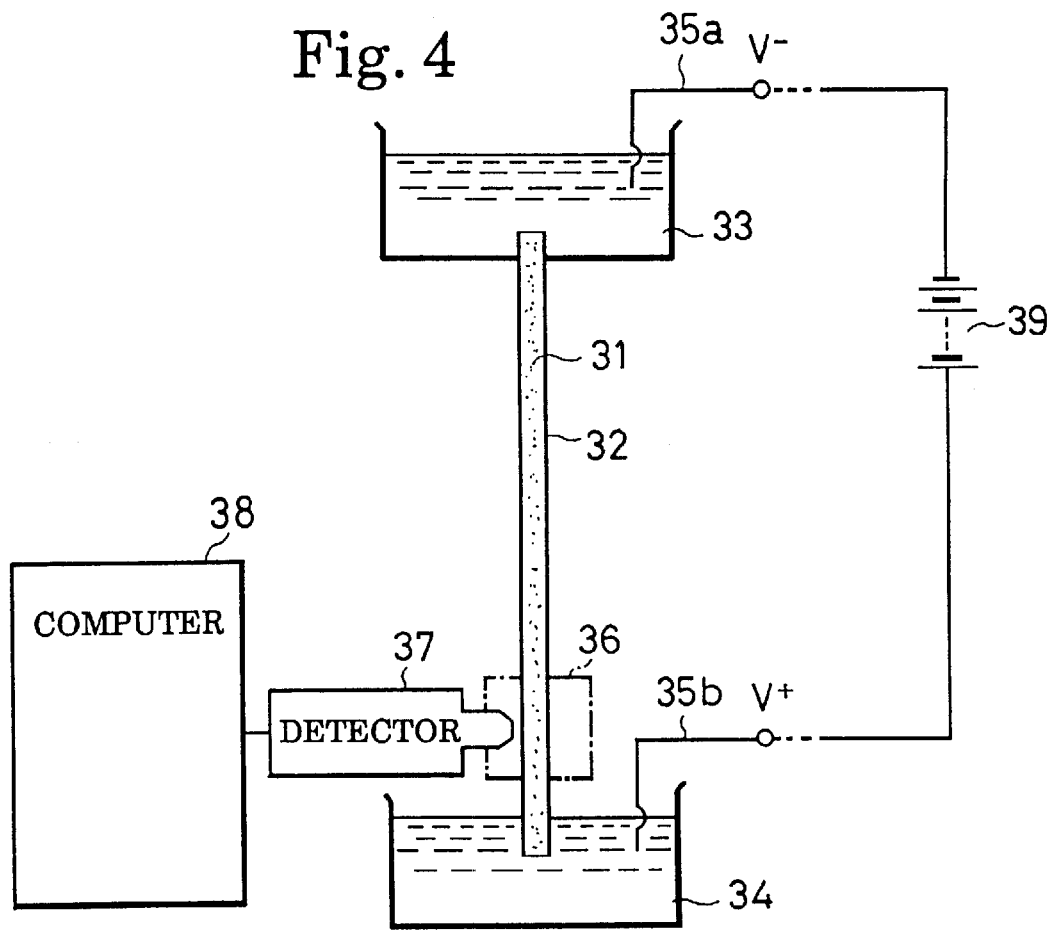
FIG. 4 is a schematic block diagram showing a gel electrophoresis apparatus for describing the method for the detection of a gel electrophoresis pattern by the fluorescence detection method.
Figure 5:
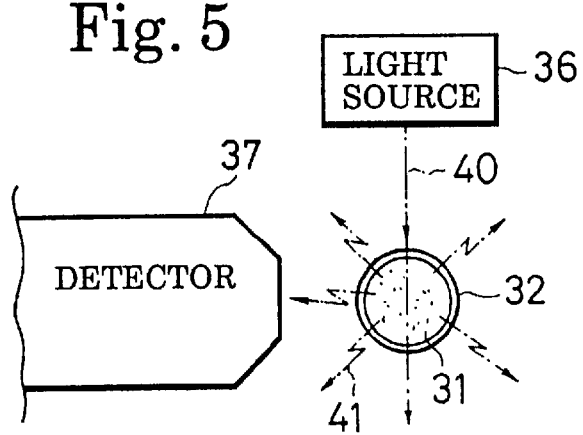
FIG. 5 is a schematic representation showing the details of a portion of a fluorescence detecting section of the gel electrophoresis apparatus for describing the method for the detection of a gel electrophoresis pattern by the fluorescence detection method.

FIGS. 3a and 3b show the results of experiments that illustrate a variation in the intensity of fluorescence relative to the progress of time when a reference marker and a DNA sample are subjected to electrophoresis, respectively, for preparing an electrophoresis pattern.

In the experiment which provided the results as shown in FIG. 3a, the DNA fragment prepared by digesting λ-DNA with a restriction enzyme Hind III was employed as a marker, and ethdium homodimer was employed as a pigment.

FIG. 3b shows the results of the variation of the fluorescent intensity relative to the progress of time, obtained by electrophoresing the sample prepared by digesting M13mp18 DNA with a restriction enzyme Bsp1286I and using diazole yellow homodimer as the pigment. From the experiments, it was found to be easy to label the fluorescent substance with the labelling substance so that the labelled fluorescent substance can readily be applied to DNA double strands.

In the embodiment of this invention as described hereinabove, as no fluorescence can be detected until the sample is discharged from the terminal end of the electrophoresis gel unit, the electrophoresis is carried out at a high speed at the initial stage of electrophoresis by applying an elevated voltage to the sample. As the electrophoresis apparatus of a capillary type is so small in the transverse cross-sectional area of the electrophoresis gel unit, an electric current is about several mA even though the voltage is elevated. Further, the electrophoresis apparatus according to the present invention has its electric power source arranged so as to make the electrophoresis voltage variable, so that DNA fragments having a large size can be separated at a relatively high speed by gradually increasing the electrophoresis voltage. This function is particularly effective for controlling the band intervals of the DNA so as to become constant.

As described hereinabove, the apparatus and the method for reading the gel electrophoresis pattern in accordance with this invention can detect the fluorescence emission from the fluorescent substance labelled in the sample with a high signal-to-noise ratio and without causing the fluorescence to scatter, which is depart from the prior art because the use of laser light sources for emitting the fluorescence from the fluorescent substance labelled in the sample is not required. Further, the electrophoresis apparatus according to the present invention can be structured less expensively because the expensive laser light source is not required.

What is claimed is:

1. A method for reading a gel electrophoresis pattern, comprising:

supplying a sample labelled with a fluorescent substance into an electrophoresis gel unit at an inlet side thereof;

subjecting said sample to electrophoresis by applying an electrophoresis voltage to said electrophoresis gel unit in order to separate said sample from said electrophoresis gel unit;

discharging said sample separated from said electrophoresis gel unit into a carrying fluid from an outlet side of said electrophoresis gel unit;

admixing said carrying fluid with a luminous liquid; and receiving fluorescence emitting from said sample contained in said carrying fluid after said carrying fluid containing said sample has been transferred a predetermined distance.

2. A method for reading a gel electrophoresis pattern as claimed in claim 1, wherein the sample contains a nucleic acid.

3. A method for reading a gel electrophoresis pattern as claimed in claim 1, wherein the supplying step is performed to supply the sample to said inlet side of said electrophoresis gel unit together with a buffer solution that has a composition substantially equivalent to or similar to a composition of said carrying fluid.

4. A method for reading a gel electrophoresis pattern as claimed in claim 1, wherein said discharging step is performed to discharge said sample separated from said electrophoresis gel unit continually into said carrying fluid.

5. A method for reading a gel electrophoresis pattern as claimed in claim 1, wherein said receiving step includes the step of passing said sample contained in said carrying fluid through a fine tube that turns upward and downward alternately in front of a photoelectric conversion element for receiving said fluorescence.

6. A method for reading a gel electrophoresis pattern as claimed in claim 5, wherein said passing step is performed by passing said sample contained in said carrying fluid through a fine tube having a vertical zig-zag portion for passing said sample contained in said carrying fluid upward and downward alternately in front of said photoelectric conversion element.

7. A method for reading a gel electrophoresis pattern as claimed in claim 5, wherein said passing step is performed by passing said sample contained in said carrying fluid through a fine tube having a spiral portion for passing said sample contained in said carrying fluid upward and downward alternately in front of said photoelectric conversion element.

8. A method for reading a gel electrophoresis pattern as claimed in claim 1, wherein said electrophoresis voltage is 10 kV.

9. An apparatus for reading a gel electrophoresis pattern, comprising:

an electrophoresis gel unit for carrying out electrophoresis therein;

a first fine tube filled with said electrophoresis gel unit;

a buffer solution container for storing a buffer solution, disposed so as to come into contact with each end portion of said electrophoresis gel unit;

an electrode disposed so as to come into contact with said buffer solution stored in said buffer solution container;

a power source for applying an electrophoresis voltage to said electrode;

a second fine tube for transferring a sample electrophoresed in and separated from said electrophoresis gel unit;

a third fine tube for supplying a luminous liquid;

a mixer for admixing a liquid containing said sample and buffer solution supplied from said second fine tube with a liquid containing said luminous liquid supplied from said third fine tube to give a mixture;

a fourth fine tube for transferring said mixture and reacting said sample with said luminous liquid for a period of time long enough to emit fluorescence to a predetermined level of intensity;

a fluorescence detecting means disposed at a terminal end portion of said fourth fine tube for detecting fluorescence emitted from said mixture; and a data processing unit for processing electrical signals converted from the fluorescence detected by said fluorescence detecting means;

wherein said fluorescence detecting means includes a photoelectric conversion element that detects the fluorescence emitted from the mixture, and wherein in said fluorescence detecting means, said fourth fine tube turns upward and downward alternately in front of the photoelectric conversion element.

10. An apparatus for reading a gel electrophoresis pattern as claimed in claim 9, wherein said fourth fine tube has a vertical zig-zag portion in said fluorescence detecting means.

11. An apparatus for reading a gel electrophoresis pattern as claimed in claim 9, wherein said fourth fine tube has a spiral portion in said fluorescence detecting means.

12. An apparatus for reading a gel electrophoresis pattern, comprising:

an electrophoresis gel unit for carrying out electrophoresis therein;

a first fine tube filled with said electrophoresis gel unit;

a buffer solution container for storing a buffer solution, disposed so as to come into contact with each end portion of said electrophoresis gel unit;

an electrode disposed so as to come into contact with said buffer solution stored in said buffer solution container;

a power source for applying an electrophoresis voltage to said electrode;

a second fine tube for transferring a sample electrophoresed in and separated from said electrophoresis gel unit;

a third fine tube for supplying a luminous liquid;

a mixer for admixing a liquid containing said sample and buffer solution supplied from said second fine tube with a liquid containing said luminous liquid supplied from said third fine tube to give a mixture;

a fourth fine tube for transferring said mixture and reacting said sample with said luminous liquid for a period of time long enough to emit fluorescence to a predetermined level of intensity;

a fluorescence detecting means disposed at a terminal end portion of said fourth fine tube for detecting fluorescence emitted from said mixture; and a data processing unit for processing electrical signals converted from the fluorescence detected by said fluorescence detecting means;

wherein said first fine tube has an outlet at a bottom end of the electrophoresis gel unit through which said electrophoresed sample is separated from said electrophoresis gel unit, and wherein said electrode is further disposed above the bottom end of said electrophoresis gel unit to prevent gases from accumulating at the outlet of said first fine tube.

13. An apparatus for reading a gel electrophoresis pattern, comprising:

a sample supplying means for supplying a sample labelled with a fluorescent substance to an inlet side of an electrophoresis gel unit;

electrophoresis means for subjecting the sample to electrophoresis by applying an electrophoresis voltage to the electrophoresis gel unit;

a fine tube in said electrophoresis gel, said fine tube having an outlet at a bottom end of the electrophoresis gel unit;

carrying means for withdrawing the electrophoresed sample from the outlet of said fine tube into a carrying fluid and carrying the carrying fluid a predetermined distance;

mixing means for mixing the electrophoresed sample and carrying fluid with a luminous liquid;

light receiving means for receiving fluorescence emitted from the sample in the luminous liquid in a position in which the carrying fluid has been carried a predetermined distance;

bypassing means for discharging gases produced at an electrode disposed at the outlet side of the electrophoresis gel unit without passing through a path through which the carrying fluid flows;

wherein said bypassing means includes disposition of said electrode at the outlet side of the electrophoresis gel unit and above the bottom end of the electrophoresis gel unit, to prevent said gases produced at said electrode from accumulating at the outlet of said fine tube.

14. An apparatus for reading a gel electrophoresis pattern, comprising:

a sample supplying means for supplying a sample labelled with a fluorescent substance to an inlet side of an electrophoresis gel unit;

electrophoresis means for subjecting the sample to electrophoresis by applying an electrophoresis voltage to the electrophoresis gel unit;

carrying means for withdrawing the electrophoresed sample from an outlet side of the electrophoresis gel unit into a carrying fluid and carrying the carrying fluid a predetermined distance;

mixing means for mixing the electrophoresed sample and carrying fluid with a luminous liquid; and light receiving means for receiving fluorescence emitted from the sample in the luminous liquid in a position in which the carrying fluid has been carried a predetermined distance; and wherein said light receiving means includes a fluorescence detecting section having a fine tube for passing the sample in the luminous liquid alternately upward and downward in front of a photoelectric conversion element that receives the fluorescence emitted from the sample.

15. An apparatus for reading a gel electrophoresis pattern as claimed in claim 14, wherein said fine tube has a vertical zig-zag portion for passing the sample in the luminous liquid alternately upward and downward in front of said photoelectric conversion element.

16. An apparatus for reading a gel electrophoresis pattern as claimed in claim 14, wherein said fine tube has a spiral portion for passing the sample in the luminous liquid alternately upward and downward in front of said photoelectric conversion element.

* * * * *